(12) United States Patent
Bromberg et al.

(10) Patent No.: US 7,105,808 B2
(45) Date of Patent: Sep. 12, 2006

(54) PLASMA ION MOBILITY SPECTROMETER (75) Inventors: Leslie Bromberg, Sharon, MA (US); Kamal Hadidi, Somerville, MA (US); Daniel R. Cohen, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/865,548

(22) Filed: Jun. 10, 2004

(65) Prior Publication Data

US 2005/0205775 A1 Sep. 22, 2005

Related U.S. Application Data

(60) Provisional application No. 60/550,640, filed on Mar. 5, 2004.

(51) Int. Cl.
*B01D 59/44* (2006.01)
*H01J 49/00* (2006.01)

(52) U.S. Cl. .................. 250/287; 250/287; 250/281

(58) Field of Classification Search ............ 250/287, 250/281
See application file for complete search history.

(56) References Cited

U.S. PATENT DOCUMENTS

| | | | | |
|---|---|---|---|---|
| 4,680,467 A | * | 7/1987 | Bryson et al. | 250/305 |
| 4,855,595 A | | 8/1989 | Blanchard | 250/287 |
| 5,021,654 A | * | 6/1991 | Campbell et al. | 250/287 |
| 5,256,854 A | | 10/1993 | Bromberg et al. | 219/121.52 |
| 5,420,424 A | | 5/1995 | Carnahan et al. | 250/287 |
| 5,534,824 A | * | 7/1996 | Nalos et al. | 331/81 |
| 5,572,022 A | * | 11/1996 | Schwartz et al. | 250/282 |
| 5,801,379 A | * | 9/1998 | Kouznetsov | 250/286 |
| 5,969,349 A | | 10/1999 | Budovich et al. | 250/286 |
| 6,052,401 A | * | 4/2000 | Wieser et al. | 372/74 |
| 6,429,426 B1 | | 8/2002 | Döring | 250/288 |
| 6,448,568 B1 | * | 9/2002 | Allen et al. | 250/492.24 |
| 6,586,729 B1 | | 7/2003 | Döring | 250/287 |
| 6,812,647 B1 | * | 11/2004 | Cornelius | 315/111.41 |

OTHER PUBLICATIONS

I. A. Buryakov, E. V. Krylov, E. G. Nazarov, U. K. Rasulev, "A New Method Of Separation Of Multi-Atomic Ions By Mobility At Atmospheric Pressure Using A High-Frequency Amplitude-Asymmetric Strong Electric Field," *Int. J. Mass Spectrom. Ion Processes* 128: 143-148 (1993).

H.-R. Döring, et al., "VIP Sources for Ion Mobility Spectrometry," *9th International Conference on Ion Mobility Spectrometry*, ISIMS 2000 Programme, IJIMS 3(2000), Halifax, Nova Scotia, Canada, Aug. 13-16, 2000.

R.W. Purves, R. Guevremont, S. Day, C.W. Pipich, M.S. Matjaszczyk, "Mass Spectrometric Characterization Of A High-Field Asymmetric Waveform Ion Mobility Spectrometer," *Review of Scientific Instruments* 69 (12): 4094-4105 (1998).

(Continued)

*Primary Examiner*—John R. Lee
*Assistant Examiner*—Jennifer Yantorno
(74) *Attorney, Agent, or Firm*—Choate, Hall & Stewart, LLP (57) ABSTRACT

Ion mobility spectrometer. The spectrometer includes an enclosure for receiving a sample therewithin and an electron beam window admits an electron beam into the enclosure to ionize the sample in an ionization region. A shutter grid is spaced apart from the ionization region and means are provided for sample ion preconcentration upstream of the shutter grid. The ion preconcentration is effective to reduce space charge resulting in a lowered threshold detection level.

36 Claims, 7 Drawing Sheets

OTHER PUBLICATIONS

G. A. Eiceman, E. G. Nazarov, and J. E. Rodriguez, J. A. Stone, "Analysis of a drift tube at ambient pressure: Models and precise measurements in ion mobility spectrometry", *Review of Scientific Instruments* 72(9): 3610-3621 (2001).

* cited by examiner

FIG. 5(a) (from Figure *** (c2))

PLASMA ION MOBILITY SPECTROMETER

This application claims priority to Provisional Patent Application Ser. No. 60/550,640 filed Mar. 5, 2004, the contents of which are incorporated herein by reference.

BACKGROUND OF THE INVENTION

Ion Mobility spectrometers (IMS) have been developed for very sensitive monitoring of chemical species. An important application of the technology is its use to detect trace quantities of explosive material and chemical agents in compact devices. Trace ions of a subject material are separated by using the fact that the electrical mobility of different ion species is different. Time of flight measurements are made. Once chemical species are separated, the ionic current is measured using an electrometer.

Presently, most IMS devices use for ionizing a sample either a radioactive source ($Ni^{63}$ being the most common, although $T^3$ and $Am^{241}$ are also used), UV or corona discharge. Use of more intense ionization sources could be advantageous, since the current measured by the electrometer would be larger, decreasing the detection threshold. If limited by ion recombination, the density of reactive ions (and therefore the current) is proportional to the square root of the ionization source. Increasing the ionization rate by a factor of one-thousand increases concentration of reactive ions (primary ions) by a factor of approximately thirty, which should result in a decrease in the minimum detectable limit (MDL) by a factor of thirty or higher. Moreover, there are cases (where the ions quickly form cluster ions, for example) where the ion loss is not determined by ion recombination. In this case, the ion concentration will be linear with ionization rate, and the ion concentration will be one-thousand times higher for an ionization source one-thousand times stronger.

Traditionally, the sample analyzed by IMS is on the order of a few hundred ml/min. This small sample size is partly due to the very low dose of the ionization source used in these instruments. Increasing the sample size by an order of magnitude can increase the accuracy and the sensitivity of the IMS. This increase can be achieved with the use of a more powerful ionization source such as an electron beam.

The use of more intense ionization sources for IMS has been previously considered by others. Electron beams have also been contemplated as an ionization source. In the patent literature, Vitaly Budovich (U.S. Pat. No. 5,969,349, October 1999) teaches the use of an electron beam as the ionization source. The source has a window, preferably mica, and an evacuated volume with a hot cathode or a photocathode. Hans-Rudiger Donzig (U.S. Pat. No. 6,429,426, August 2002) teaches the use of an electron beam source used to make x-rays. In this case, the electrons do not have to be extracted from the evacuated volume. More recently, Hans-Rudiger Donzig (U.S. Pat. No. 6,586,729, July 2003), teaches the use of a current controlled e-beam for the control of x-ray emission, using a sustainer (in a triode configuration). This patent also teaches a scheme for monitoring the pressure in the tube and evacuating the tube when the pressure is too high.

These patents, and in particular U.S. Pat. No. 5,969,349, teach an electron source with a cathode at a high negative potential. This high potential is needed for acceleration of the electrons using conventional acceleration technology. However, conventional technologies present issues with the size of DC power supplies (including the transformer), the size of the high voltage insulators and other issues dealing with high voltage such as arcing. Alternatives to the high voltage requirement for high energy electron beams could result in significantly more robust and compact devices.

In U.S. Pat. Nos. 5,969,349, 6,429,426 and 6,586,729, no mention is made of the possibility of using a variable strength ionization source for the optimal performance of the IMS, nor do they teach operation of IMS to handle the large space charge that is generated by a source that is much stronger than the conventional radioactive sources in IMS devices. Large space charge is not an issue with U.S. Pat. Nos. 6,429,426 and 6,586,729, due to the very low efficiency in turning electron energy into soft x-rays.

It is very important, while increasing the intensity of the ionization source, to decrease the effect of space charge in the drift region in order to take full advantage of the higher ion concentration. High space charge at the higher ion concentration limits the resolution by spreading the peaks and by ion radial loss in the drift column due to space charge.

An approach that uses nonlinear effects on mobility for chemical species separation has been proposed. This approach employs High Field Asymmetric Ion Mobility Spectrometry (FAIMS) (I. A. Buryakov, E. V. Krylov, E. G. Nazarov, U. K. Rasulev, Int. J. Mass Spectrom. Ion Processes 128 (1993) 143; R. W. Purves, R. Guevremont, S. Day, C. W. Pipich, M. S. Matyjaszczyk, Rev. Sci. Instrum. 69 (1998) 4094.)). See also, U.S. Pat. No. 5,420,424, ION MOBILITY SPECTROMETER, BL Carnahan, A. Tarassov Apr. 29, 1995. In this case, the ion separation occurs by applying a combination of DC and AC fields in the direction perpendicular to the motion of the sample gas flow. The ions are separated due to nonlinearity of the ion speed with respect to the applied electric field. A combination of DC and AC fields results in no net drift for a specific set of ions, which after separation can thus be injected into a mass spectrometer (MS). The applied electric fields are perpendicular to the direction of gas flow, and the ions are separated/removed in the direction perpendicular to the gas flow. The advantage of this scheme is that it is possible to have continuous injection into the MS (as opposed to a regular IMS that has pulsed injection of the ions of interest, known, and the product ions). However, the separation in this approach (FAIMS/MS) occurs in the drift region, and does not solve the problem of high space charge.

Alternative methods for concentrating the ions were discussed by William Blanchard (U.S. Pat. No. 4,855,595, August 1989). This patent teaches the concentration of the sample ions using electric fields in the drift region, downstream from the shutter. The issue of high space charge in the region upstream from the shutter is not addressed, nor is any preconcentration or space charge reduction upstream from the shutter. The problem is not resolved by concentrating in the drift region, since the largest space charge occurs immediately after the shutter grid, before the ions have had time to axially separate.

Figures 1A, 1B:
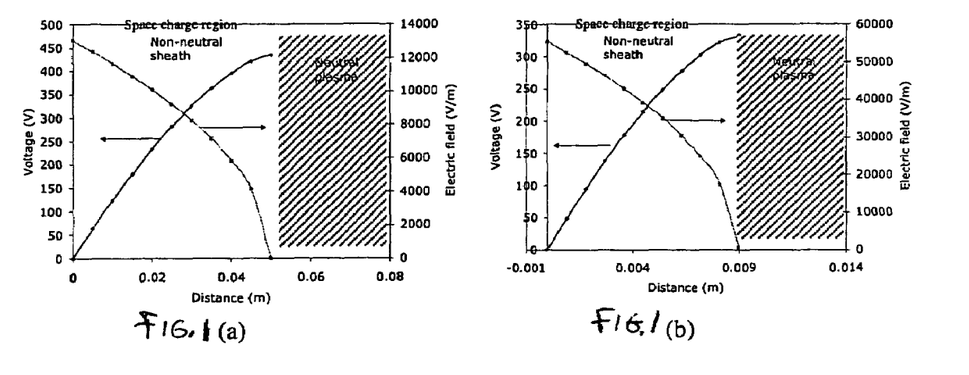

A model for the sheath region has been developed. The sheath region is defined as the region where species of either positive or negative charge exist, surrounding a region with very similar positive and negative ion concentrations. Results are shown in FIGS. 1a and 1b. For the case of 2 nA (FIG. 1a) (typical of present day devices with a current density on the order of $10^{-5}$ $A/m^2$) the dimension of the space charge region (known as sheath) upstream from the shutter can be on the order of a few centimeters (IMS design used for the calculations was obtained from *Analysis of a drift tube at ambient pressure: Models and precise measurements in ion mobility spectrometry*, G. A. Eiceman, E. G.

Nazarov, and J. E. Rodriguez, J. A. Stone, *Review of Scientific Instruments* 72 3610 (2001)). The distance between the shutter and the ionization region in conventional IMS systems is comparable to the sheath dimension. For this reason, these systems are not strongly affected by space charge in the ionization region. The electric field is strongest in the zone next to the shutter grid, and approaches zero at the location of the plasma zone.

If the ionization strength is increased, the sheath size is reduced. Results for the case of current density on the order of 200 nA are shown in FIG. 1b. In this case, the size of the sheath is less than 1 cm. Space charge is important in this case, and care must be taken in the latter case with the ion injection method to minimize space charge in the drift region. Conventional injection methods would result in space-charge dominated flow in the drift region, with loss of resolution and corresponding increase in Minimum Detection Level.

Present day devices utilize a relatively low radioactive source, about 10 mC (milliCuries). This ionization source produces high energy electrons with a current of about 15 pA (picoAmperes). It should be noted that these fast electrons ionize the background gas producing a swarm of electron/ion pairs, at an energy expense of ~35 eV per electron/ion pair. With little difficulty it is possible to have an electron beam with currents of a few μA (microA), while with difficulty it is possible to have electron currents on the order of mA (milliA). This results in a very large increase in the ionization source, about 5 orders of magnitude for the case with a 1 μA (microA) beam. It should be noted that alternative ionization sources in otherwise conventional IMS devices (such as corona discharge) operate at currents on the order of a μA (microA).

In the drift region, the space charge limits the resolution of the instrument. With 2 nA current in the drift region, present day IMS have substantial space charge to result in substantial spreading of the ion cloud (and therefore loss of resolution and selectivity). With a 100 μs pulse width (corresponding to an axial cloud length of the about 1 mm), a 2 nA beam will spread about 50 μs (corresponding to about 0.5 mm axial length of the cloud). Therefore, space charge in the drift region is already important in present day devices, and needs to be addressed for devices with much higher ionization rate for improved resolution in present day devices.

Diffusion of the ions is another source of broadening. It has been known that the resolution (selectivity) limitation due to diffusion depends on the voltage applied across the drift region. For the highest voltages considered, diffusion is less important, and the spreading is the combined effect of both space charge and diffusion.

Although a large amount of literature exists on IMS devices, little is said about ion handling upstream from the shutter. In this region, high space charge results in plasma surrounded by sheaths. Improved performance of the IMS can be obtained by using innovative methods of ion injection into the drift region, including shutter grid design.

Figures 2A, 2B:
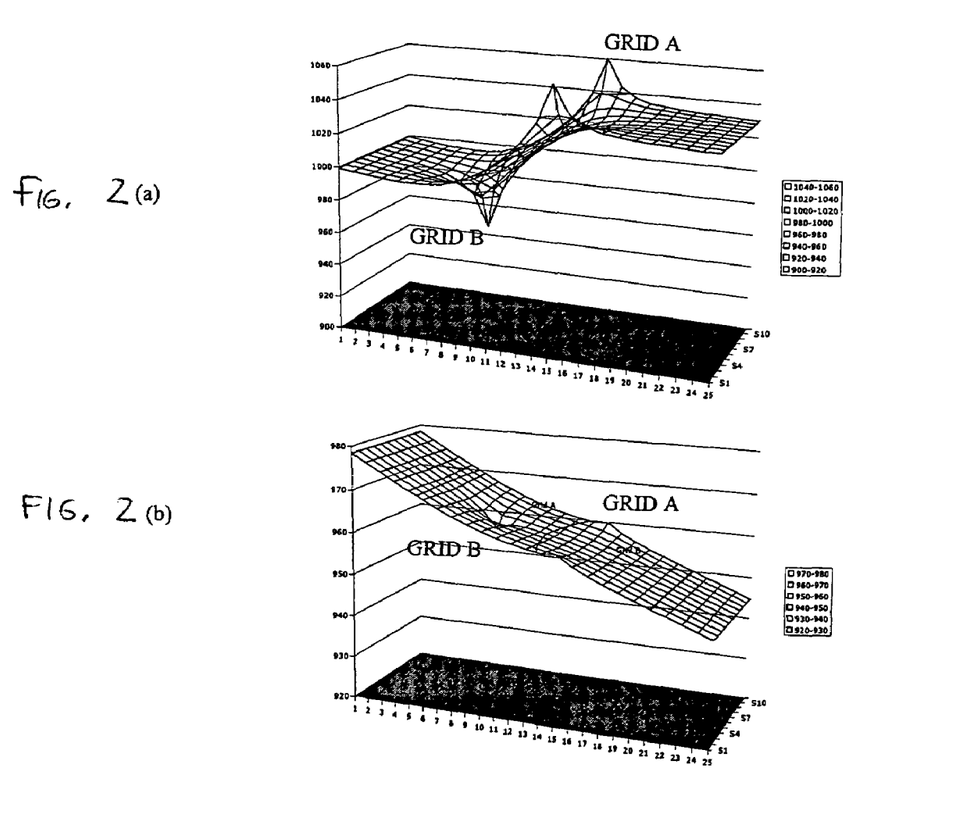
FIGS. 2a and 2b are graphs of potential distribution, without space charge, for a shutter grid region within a conventional ion mobility spectrometer (a) when positive ions are shut off from the drift region and (b) when positive ions are being admitted to the drift region (potentials for Grid A and Grid B are the same).

FIG. 2a shows the potential distortion, due to finite geometry effects, in the shutter region for those conditions with the shutter closed. FIG. 2b shows the electric field with the shutter open (data from Eiceman et al.). The ion reaction region is to the left of the shutter, while the drift region is to the right. The grid spacing and wire size were taken from Eiceman (0.05 mm parallel wires separated 0.5 mm). Spikes occur at the location of the parallel wires. Note the large distortion of the potential due to shutter grid geometry, and in particular, that the potential to repel the positive ions is substantially less than the applied potential. It is during transients (i.e., when the shutter is open) that the distortion effects are important in accepting ions. This is important because the ions are extracted mainly from the regions with large field distortion (the width of the cloud is about 1 mm, and the region of highly distorted fields is about 0.5 mm).

SUMMARY OF THE INVENTION

In one aspect, the invention is an ion mobility spectrometer having an enclosure for receiving a sample therewithin. The spectrometer includes an electron beam window for admitting an electron beam into the enclosure to ionize the sample in an ionization region. A shutter grid is spaced apart from the ionization region and means are provided for sample ion preconcentration upstream of the shutter grid. It is preferred that the ion preconcentration be effective to reduce space charge resulting in a lowered threshold detection level.

In order to prevent very large space charge in the region upstream from the shutter in a preferred embodiment, the electron beam is pulsed in a manner to ionize the background and sample. Pulse ionization allows the possibility of diluting the space charge. High mobility ions reach the shutter first (because of higher diffusivity and mobility). The ions of interest reach the shutter later. Chemistry occurs throughout the region, though. By pulsing the electron beam with a varying duty cycle additional discrimination and dynamic range are gained. The time of chemistry can be varied, as well as the concentration of ions in the ion cloud produced by the pulsing electron beam.

In a preferred embodiment, the means for providing ion preconcentration comprises a varying electric field upstream from the shutter grid. In one embodiment, at least one preconcentration grid upstream of the shutter establishes the varying electric field. A plurality of preconcentration cells is also preferred.

The varying electric field may be an asymmetric field such as an asymmetric square wave (a periodic signal whose voltage is varied from positive to negative, with unequal positive and negative voltages, and/or different times during which the positive or the negative ions are applied). It is preferred that the asymmetric field be selected to optimize ion preconcentration. It is also preferred that timing of opening of the shutter grid is synchronized with the varying electric field. It is also preferred that the shutter grid be opened when sample ions are closest to the shutter grid. It is preferred that the grid include grid wires having a characteristic size and spacing less than the spacing between grids. It is preferred that the grids be a 2-dimensional pattern, fabricated using microfabrication or microlithographic techniques. Smaller feature sizes result in reduced distortion of the electric fields in the region upstream from the shutter and the preconcentrator, and improved introduction of the ion cloud to the shutter or to the preconcentrator.

In a preferred embodiment, the electron beam comes from a source using resonant acceleration of electrons. The resonant acceleration may come from cyclotron motion of electrons in a magnetic field. Such magnetic field may be produced by a permanent magnet. The electron beam source may employ an RF source in the range of 500 MHz to 15 GHz. It is preferred that the electron beam be collimated such as by vanes. It is also preferred that the electron beam come from a source having a cold emission cathode. Suitable electron beam windows are made of low Z materials with high thermal conductivity such as diamond or sapphire.

In yet another aspect, the invention is an ion mobility spectrometer having an enclosure for receiving a sample therewithin. Means are provided for ionizing the sample and an electric field optimizes the ionization process. In a preferred embodiment, the electric field changes the energy of secondary electrons produced by an electron beam, and thus varies the chemistry between these electrons and the background and sample gas. In yet another embodiment, the electric field changes the energy of secondary electrons produced by a radioactive source. In yet another embodiment, the electric field changes the energy of secondary electrons produced by an ultraviolet ionization source. It is preferred that the electric field in the ionization region have a value in the range of 0.8 to 8 Townsends. The electric fields in these embodiments can be DC or AC. For the field to penetrate into this region, low concentration of ions is required.

In the above embodiments, quantification of sample ion concentration is determined from dependence of sample ion current on the strength of the ionization source. The ionization source can be varied by changing the current of the electron beam, or by changing the duty cycle of a pulsing electron beam. Alternatively, quantification of sample ion concentration is derived from the saturation of sample ion current.

BRIEF DESCRIPTION OF THE DRAWING

FIGS. 1a and 1b are graphs of electric field and potential versus distance within a conventional ion mobility spectrometer (IMS). FIG. 1(a) has currents comparable to present day devices, 2 nA and FIG. 1(b) has current increased to 200 nA.

FIGS. 7a and b are schematic diagrams of voltage applied to preconcentration cell regions in the IMS apparatus of the invention. FIG. 7a shows constant potential after switching, while FIG. 7b shows variable potential (ramp-like) after switching.

DESCRIPTION OF THE PREFERRED EMBODIMENTS

High energy electron beams have been proposed for use with an IMS (VIP Sources for Ion Mobility Spectrometry H.-R. During, G. Arnold1, V. L. Budovich, Bruker Saxonia Analytik GmbH, Leipzig, Germany and CHROMDET ANALYTICAL INSTRUMENTS, Moscow, Russia). The advantages of using electron beams are pulsed operation, high instantaneous and average currents (related to dose rates) and capability for varying the current. The use of high current dose rate results in high reactive ion density. A high reactive ion density is good in that it is possible to decrease the Minimum Detection Limit (MDL), by ionizing a larger fraction of the molecules of interest. However, to our knowledge, the advantage of using e-beam ionization has not ever been realized. The apparent failure to realize this advantage may be due to space charge effects in the drift region. Conventional IMS devices, as well as an e-beam enhanced one, are shown in FIGS. 3a and 3b.

Figure 3A:
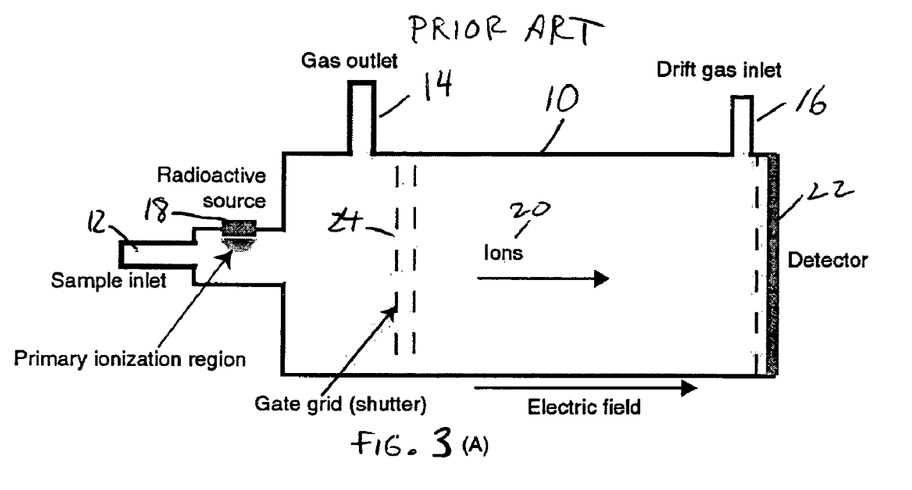
FIG. 3a. is a schematic illustration of a prior art conventional IMS.

A conventional, prior art ion mobility spectrometer is shown in FIG. 3a. An ion mobility spectrometer 10 includes a sample inlet 12, a gas outlet 14 and a drift gas inlet 16. A radioactive source 18 generates ions 20 that encounter a detector 22. A gate grid or shutter 24 is also provided.

Figure 3B:
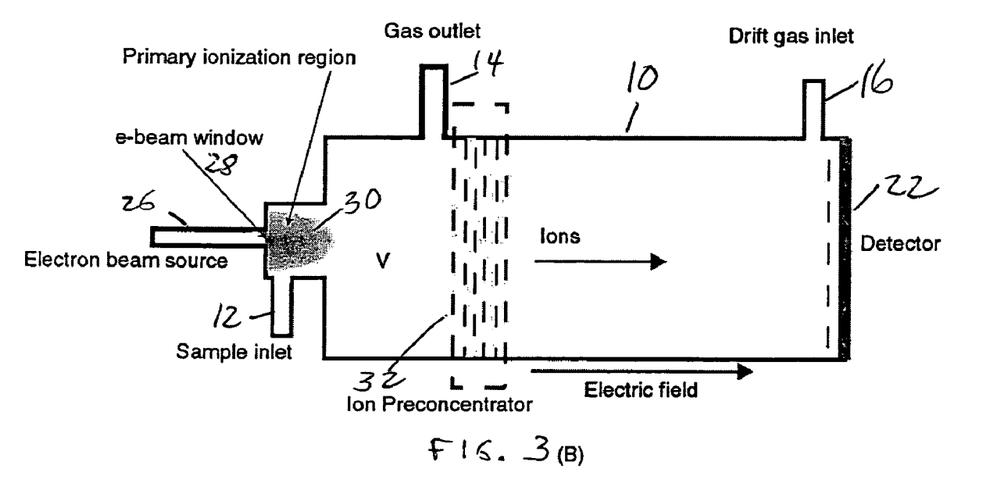
FIG. 3b. is a schematic illustration of an e-beam enhanced IMS with electron beam and preconcentrating grid.

An embodiment of the ion mobility spectrometer according to the present invention is shown in FIG. 3b. Instead of a radioactive source 18, an electron beam source 26 is provided. The electron beam passes through an e-beam window 28 into a primary ionization region 30. As will be described more completely below, the spectrometer of the invention includes an ion pre-concentrator 32.

A preferred embodiment involves an electron beam that would not have the drawbacks of high voltage. The possibility of miniaturizing the device is severely compromised by the use of high voltage (feedthroughs are heavy, transformer need high voltage dielectric, which makes them large and heavy). At the same time, high energies are desirable. With high energies, it is possible to increase the thickness of the window through which the electrons need to flow, easing the vacuum tightness issues. In addition, the high energy results in increased penetration length of the electrons into the sample gas. The requirements can be met by the use of RF acceleration. Three types of accelerators can be considered: the first one uses cyclotron resonance in a magnetic field (electron cyclotron), the second one uses linear accelerators (LINAC), and the third one incorporates a high voltage transformer inside an evacuated cavity where the electron beam is being produced.

The first one, the electron cyclotron accelerators, can be made by the use of an RF cavity, a microwave source, a low field magnet, a high vacuum tube and appropriate electron injection. Thus, if an evacuated cavity is placed in a ~300 Gauss field, with electron injection at a point or line location, the electrons would be continuously accelerated by the application of an RF field at 900 MHz. At this frequency, high efficiency, high power, solid state, components exist. The electrons are extracted from the source at relatively high energy, using the fact that as the energy of the electrons increases, the gyro radius of the electron motion increases.

The window location would therefore determine the energy of the extracted electrons. Such a device would trade off the high voltage for the requirement of a low field permanent magnet and compact, high efficiency amplifier module (with powers on the order of about 10 W).

The second source, the electron LINAC, uses an RF cavity, with proper injection of the electrons, to provide acceleration. The RF cavity should be replaced with a slow wave structure because of the low velocity of the electrons with respect to the speed of light.

The third electron source avoids the need of the high voltage feedthrough and the transformer dielectric requirements by operating the transformer at high frequencies and in vacuum. The current can be limited by the use of a photocathode. This unit has to be operated in a pulsed mode, since the accelerating voltage reverses direction. The frequency of the power supply can be adjusted to match the optimal ionization rate.

The material of the electron beam extraction window needs to satisfy multiple requirements. It has to be non-permeable to gases to maintain the vacuum, strong enough so that it can support the large pressure differential (atmospheric on one side and vacuum on the other), and has to have high thermal conductivity in order to remove the heat deposited by the electrons. The material should be such that electron loss energy in the window is minimized. It has to be thin to maximize transmission, but thick enough for preventing gas permeation. If it is very thin, it needs to be supported by a high transparency "hibachi" type grid to minimize stress and strains. Low-Z materials such as epitaxially grown diamond, beryllium and sapphire are attractive window materials (high thermal conductivity, made with low-Z materials and high strength).

Not described in U.S. Pat. Nos. 5,969,349, 6,429,426 and 6,586,729 is the use of cold field emission cathodes. The use of a thermal emission cathode is unattractive. The thermoionic cathode requires a power supply at high voltage requiring substantial power. A cold emission cathode is thus very attractive for the present application. The photocathode, described in U.S. Pat. No. 5,969,349, requires a light source, but allows for a simple way to control the current.

The difficulties associated with the space charge in the drift region can be avoided by using a preconcentrator that minimizes the ions that are not of interest (usually low mass ions with high mobility, including the reactive ions), while increasing the fraction of the product ions of interest. Thus, in the drift region mainly the product ions are injected and separated, minimizing the space charge associated with higher mobility reactive ions, a problem especially pronounced during the initial phases of the separation process. This is because directly downstream from the shutter grids the drifting ion bunches are all superimposed on each other (not separated axially), while further downstream from the shutter grid the different ions separate axially, as different ions drift with different speeds.

The desired preconcentration can be achieved by using appropriately varying electric fields in the region upstream from the shutter grids. Pulsing the electric fields in a manner that is either symmetric or asymmetric can be used to preferentially concentrate the product ions in the region of the grid.

Figure 4:
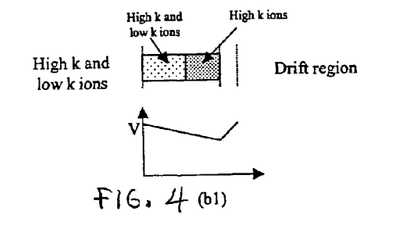
FIGS. 4a, b1, b2, c1 and c2 are schematic illustrations of ion preconcentration steps based on linear mobilities.
Figure 4A:
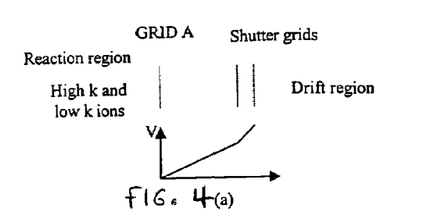

The applied fields need to be generated between multiple grids, upstream from the shutter grid. FIG. 4 shows a schematic of the process. First, grid A, upstream from the shutter grid, shuts off all positive ions, as shown in FIG. 4(a). Then grid A admits positive ions, as shown in (b1) and (b2), to the point where the slow positive ions have made it all the way to the shutter grid (b2), and some of the high mobility positive ions have been collected and neutralized by the shutter grid. At this point, the field is reversed, FIG. 4(c1) and (c2). All ions start to move back, but as shown in (c2) all fast positive ions have been removed from the regions between the grid A and the shutter grid, with only slow mobility positive ions remaining. A similar technique (with reversed electric fields) can be used to separate negative ions. Means of implementation of the multiple grids, including preferred embodiments, are discussed later in this specification.

Figure 5:
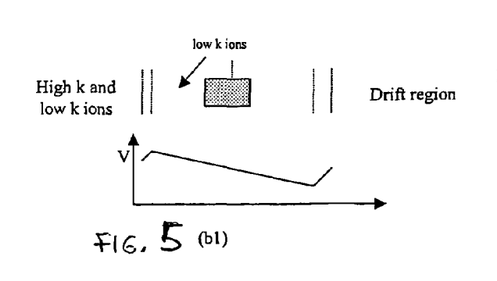
FIGS. 5a, b1 and b2 are schematic illustrations of the use of multiple preconcentration cells.
Figure 5A:
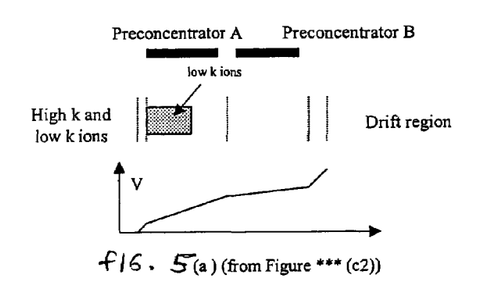

Multiple preconcentrating regions can be used. Thus, an array of grids as shown in FIG. 5 can be used to eliminate the high mobility ions from multiple regions. The case of two preconcentrating regions is schematically shown in FIG. 5. FIG. 5(a) corresponds to the end point of the preconcentration event in FIG. 4(c2). The ions are shifted in FIG. 5(b1) and 5(b2) to the preconcentration cell B from preconcentration cell A by appropriate use of electric fields. Once the ions are in the preconcentration cell B, the ions can be maintained there by appropriate oscillation of the electric field (since diffusion is small), while the preconcentrator A can be used again for separating other ions. The process can be repeated, and the ion bunches "joined" in preconcentrator B. To first order, the length of the ion bunch in preconcentrator B is equal to the final size of the ion bunch in preconcentrator A times the number the bunches that have been introduced (i.e., the bunches in preconcentrator B are concatenated, added up head-to-tail, as opposed to superimposed).

Figure 6:
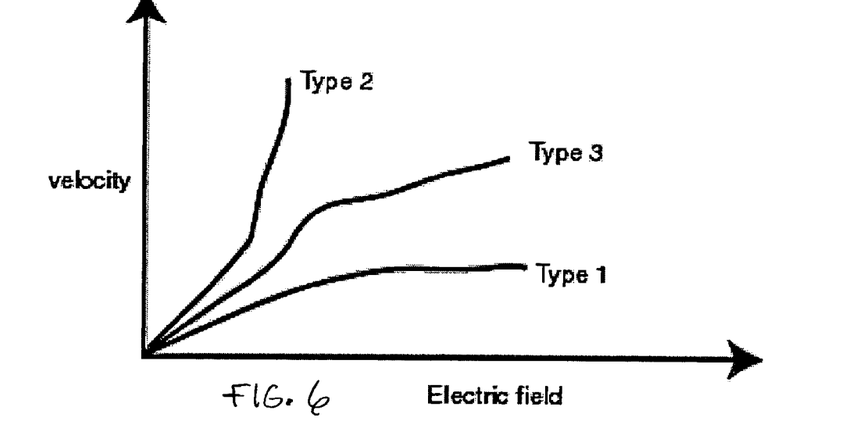
FIG. 6 is a graph of velocity versus electric field illustrating different types of nonlinear behavior of ions with respect to applied electric field.

Nonlinearity in the mobility of different ion species can be used to aid in the preconcentration. Mobility is defined as the ratio between the ion velocity and the applied electric field, and it is constant only in the region where the velocity is linear with respect to the field. A schematic of the nonlinear behavior of the ion velocities as a function of the applied electric field is shown in FIG. 6. For particles of type 1, the effective mobility decreases at the higher electric fields, while the opposite is true for ions of type 2. For ions of type 3, the effective mobility increases at the intermediate fields but then decreases at the higher fields.

For example, assume that the high mobility ions have a mobility that increases with electric field, such as ions of type 2. Then in the process of removing the high mobility ions from the preconcentration region shown in FIG. 4(c1), the fast ions move relatively faster out of the preconcentration region than moving in. The ratio $v_{fast}/v_{slow}$ is larger during the depopulation of the preconcentration region (FIG. 4(c)) than during the population time (FIG. 4(b)). As a consequence, more of the slow ions are retained in the preconcentration region.

Figure 7A:
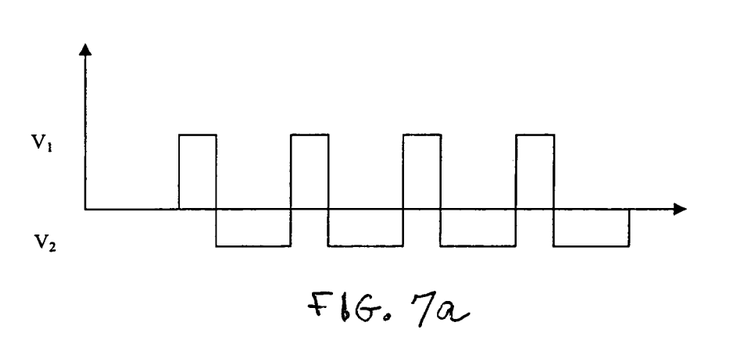
Figure 7B:
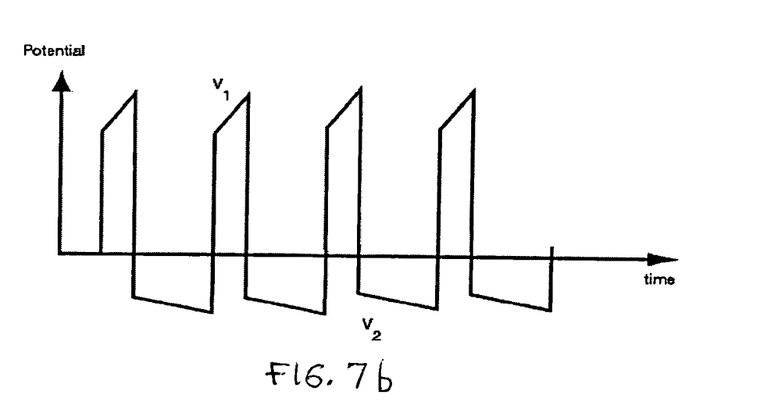

A preferred method would be to vary the electric field by applying an appropriate waveform. AC fields in this region can be used to preferentially move the reactive ions of no interest away from the region of interest next to the shutter grid. The preconcentration is thus achieved by using either linear or nonlinear mobilities of the reactive ions and the heavier ones that are of interest. The separation motion in this case is with the electric field parallel to the main direction of the ions. Although sinusoidal drive of the electric field could be used, better results can be achieved by using higher harmonics, even a non-symmetric square wave. An illustrative example is shown in FIGS. 7a and 7b. The ratio between $V_1$ to $V_2$ can be adjusted to achieve optimum preconcentration that depends on the nature of the background gas and other contaminants present in the gas stream.

It is not necessary to have the applied electric field average to 0, that is, it may be better to have a DC value to the applied electric field.

The preconcentration would move the product ions of interest to the region close to the shutter grid. If the ions were to reach the shutter grid region, the ions would strike the grid and lose their charge in the grid (the grid would collect the ions). By adjusting the frequency of the field and the shape of the waveform (positive and negative values, and average values), it is possible to have the product ions of interest move in and out of the region near the grid, avoiding the loss of most of the product ions of interest. The grid can be used to collect and neutralize the ions that are not of interest (the reactive ions).

Preconcentrating ions of interest for a finite amount of time in the preconcentrator has additional advantages. The ions can be kept there for allowing chemistry, if it is advantageous, with a well determined time. In addition, if multiple ions of close mobilities are present, asymmetric fields can be used to take advantages of non-linear mobilities to remove ions that are not of interest. Thus additional separation/selectivity can be obtained.

In addition to providing separation of the ions, the process puts the ions of interest next to the shutter grid. When the shutter is activated, only low mobility ions are accepted. Thus, the process reduces the space charge due to faster ions, which are the bulk of the ions.

Care must be taken when moving ions through a grid. In principle, the electric field strength should remain constant or increase from one cell to the next in the direction of ion motion. Decreasing the field strength from one cell to the next (or through the shutter electrode) results in substantial loss of ions. These ions are collected by the grids, and can contribute to "memory" effects in the detector. Deposition of ions on the grids can be minimized by adequate control of the electric fields, as well as improved grid design, as will be described below.

Preconcentrating the ions of interest in a very small region right next to the shutter grid will also increase the resolution of the detected peaks by decreasing the opening time of the shutter grid.

At typical operation of IMS, with shutter speeds on the order of 100–200 microseconds, the width of the ion bunch accepted into the drift region is on the order of 1 mm. Thus, no large loss of signal occurs if only a small fraction of the ions are preconcentrated, since most of the ions generated in the ionization region are lost anyway.

In order to best introduce the ions into the drift region and to minimize distortions of the potential, a 2-dimensional grid (instead of grids made from parallel wires) should be used. The grids can be made using advanced manufacturing techniques, such as rapid prototyping, micromachining or microlithography. Thus, the grids can be patterned on both sides of a substrate that is removed afterwards in the central region, but leaving the outside of grid support. Very accurate positioning of the grid elements can thus be obtained, with high transparency. Care must be taken in order to assure that the grid material ends in tension, in order to prevent buckling of the grids.

Alternatively, grids can be made with insulator support, with channels through both the conducting and insulating regions. Thus, an embodiment would involve using $SiO_2$ insulator, deposition of Si on it, followed by removal of material to make the channels, which should have a high fraction of open area. The process can be repeated with additional layers of $SiO_2$ and Si to make a grid array. The grid array could have 2-dimensional features (squares, hexagons, etc), and they can be interleaved (so that the features in the grids do not align in the axial direction). This manner allows the manufacturing of the grid arrays with well developed use of Si-based processes.

Figure 8:
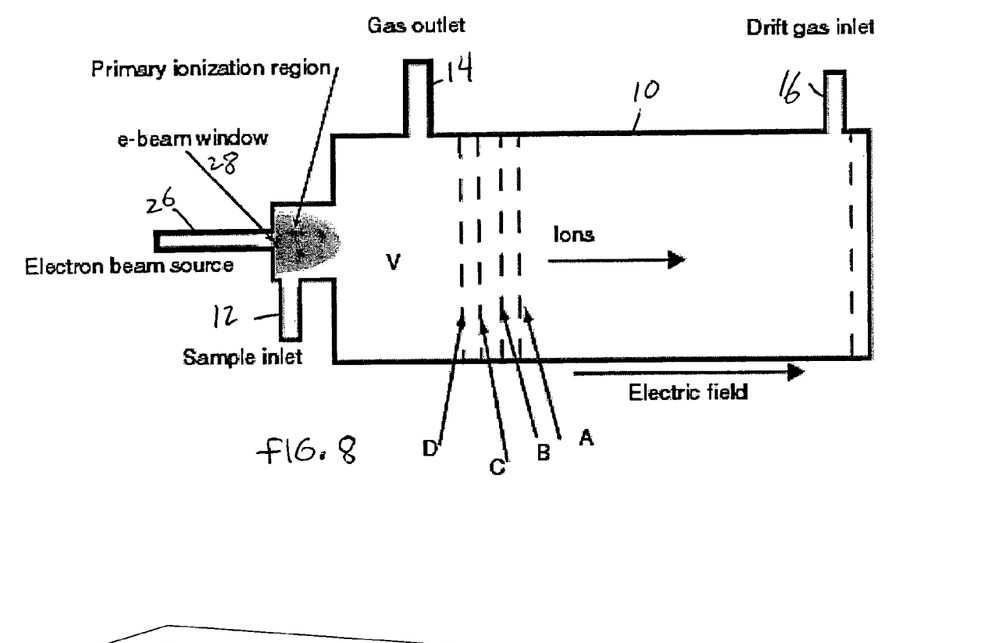
FIG. 8 is a schematic illustration of the IMS of the invention including multiple grids upstream from the shutter grids for preconcentration of ions of interest. This figure shows two grids forming a tetrode.

This IMS multigrid concept is illustrated in FIG. 8. The conventional shutter grids are shown as A and B. The other grids (two shown C and D) constitute the preconcentrating cell.

Figure 9:
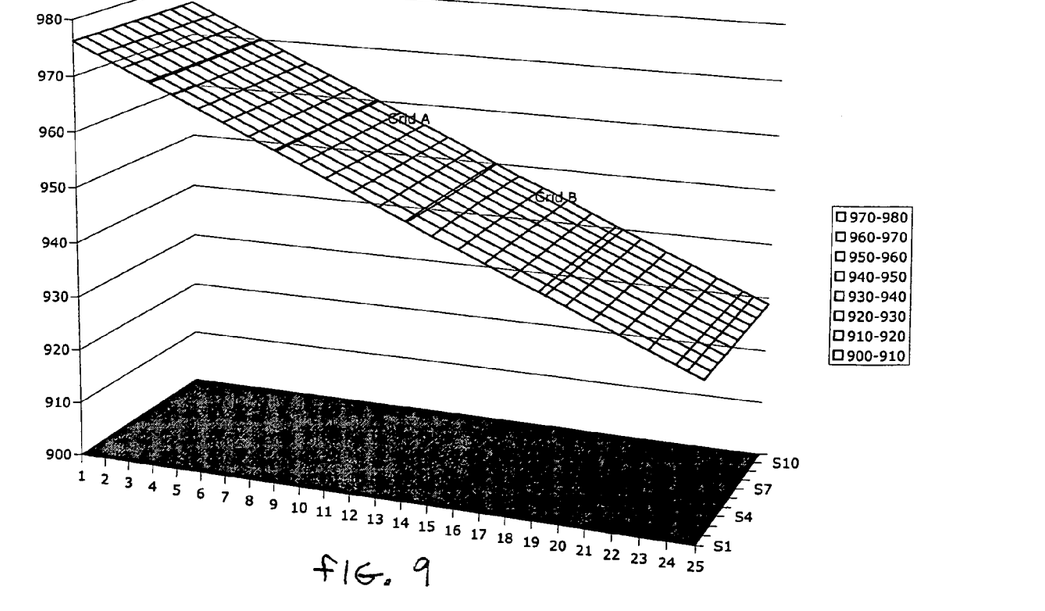
FIG. 9 is a graph illustrating the potential distribution for the case of two grids.

FIG. 9 shows the potential profile as produced by a set of grids, for a different set of voltages than those shown in FIG. 2. The grids are made of 0.05 mm parallel wires with a center-to-center wire distance of 0.5 mm. The grids are separated by 0.3 mm. The geometry is similar to that of FIG. 2, with the only difference being the applied voltages. Voltages were chosen so that the value of the electric field across Grid A is the same on both sides of the grid. As can be seen, little distortion of the electric field occurs because of finite size of the grid wires. The second grid in FIG. 2*b*, Grid B, on the other hand, has an electric field that is higher on the left than on the right hand side. The difference in electric fields results in large distortions of the field, with a large number of the electric field lines terminating in the wires that make up the grid. Thus, the presence of the grid does not much affect the potential distribution if the electric field is uniform across the grid. Thus, it would be possible to establish the drift region fields using grids, instead of rings as is the common practice. The use of grids allows for a more uniform field to be established in the drift region, and thus minimize the growth of the pulses.

In addition to the possibility of increasing the concentration of the product ions by means of a higher dose from the electron beam source, it would also be possible to selectively increase the ionization probability of a molecule of interest by tuning the energy of the secondary electrons in the background gas. This can be accomplished by using an electric field external to the electron beam (as taught by U.S. Pat. No. 5,256,854, L. Bromberg et al., *Tunable plasma method and apparatus using radio frequency heating and electron beam irradiation*).

One process of ionizing some molecules is through a dissociative ionization. This process is a function of the electron energy that attaches to the molecule. Using an external electric field, one can tune the energy of the secondary electrons generated in the background gas to the optimum electron energy needed for dissociative ionization.

Figure 10:
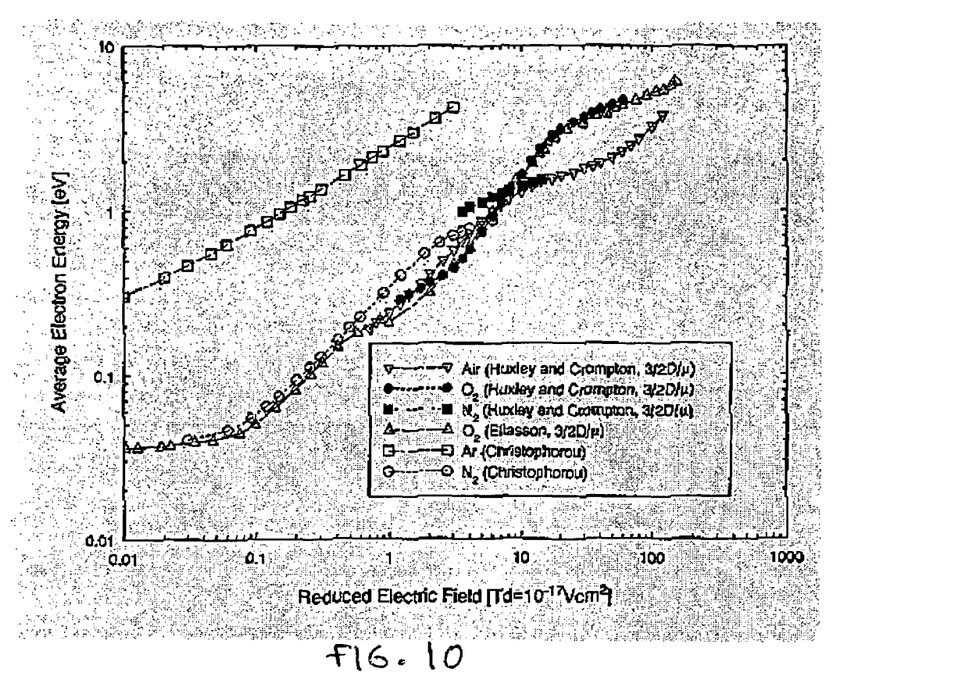
FIG. 10 is a graph of average energy of electrons as a function of reduced electric field.

The average electron energy is shown in FIG. 10 as a function of the reduced electric field (electric field divided by the concentration of neutral particles). The average electron energy may range from 0.025 eV for no electric field (corresponding to room temperature) to 4 eV for the maximum electric field achievable without electrical breakdown (corresponding to about 30 kV/cm at atmospheric pressure). For a value of the reduced electric field of 0.8–8 Townsends (Tn), the average electron energy would be approximately 0.2 eV and 1 eV, respectively.

The application of the electric field for adjusting the ionization could be used for any source of electrons. Thus it can be used for conventional radioactive sources as well as with electron beams.

The optimal "tuning" electric field for increasing the energy of the secondary electrons may be different from that optimal for preconcentrating the ions. In this case, an additional grid (or any other means of establishing an electric potential) may be used. Since the primary electrons (and therefore the secondary electrons, which are mainly present in the region where the primary electrons are) are localized to a small region next to the electron source, the "tuning" electric field needs to be generated in a small region compared with the preconcentrating and drift regions. Alternatively, the "tuning" field can be enhanced or decreased in the primary ionization region by proper shaping of the electrodes. In this case the "tuning" electric field in the primary ionization region will always be ratioed to the electric field in the preconcentrating region.

Figure 11:
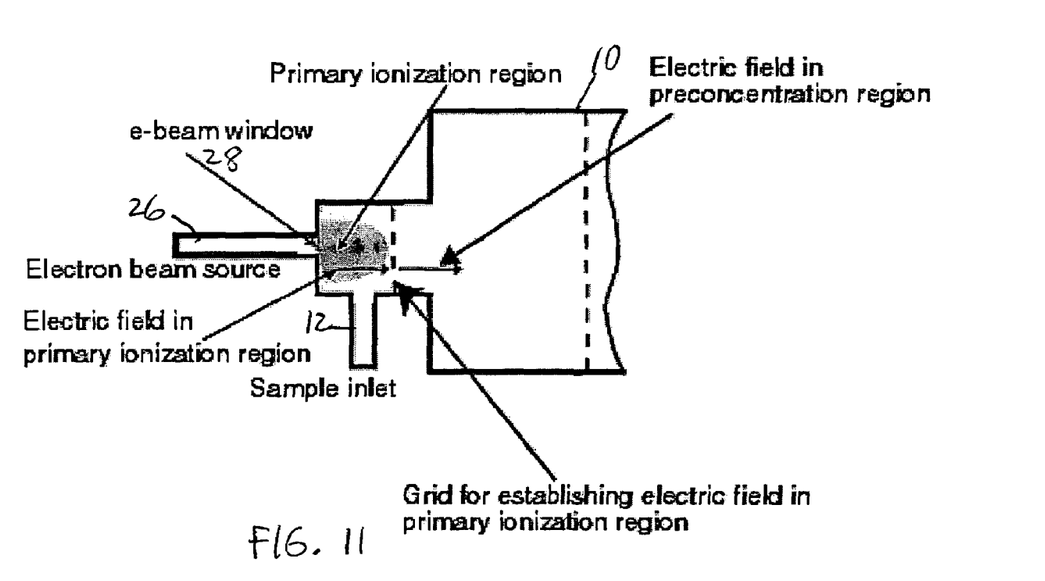
FIG. 11 is a schematic illustration showing the presence of two electric fields, one for tuning secondary electron temperature in the primary ionization region and a second field for preconcentrating ions of interest upstream of the shutter grid.

The "tuning" electric field may be DC applied, or AC in order to minimize drift of the ions (if the AC field is fast enough to prevent large drifts of the ions). The "tuning" electric field can be asymmetric, as is the case with the preconcentrating field. FIG. 11 shows an illustrative diagram with the "tuning" field in the primary ionization region along with the preconcentrating electric field. The electric fields can be applied in such a manner to prevent common mode interaction of the fields.

Use of electron sources has the advantage that the source of ionization can be modulated (turned on and off, and can be varied). Pulsing on and off is useful for synchronous detection of the ions (by using homodyne detection). The electron e-beam can be modulated and synchronized with the detector, so that any background signal can be cancelled out.

Figure 12:
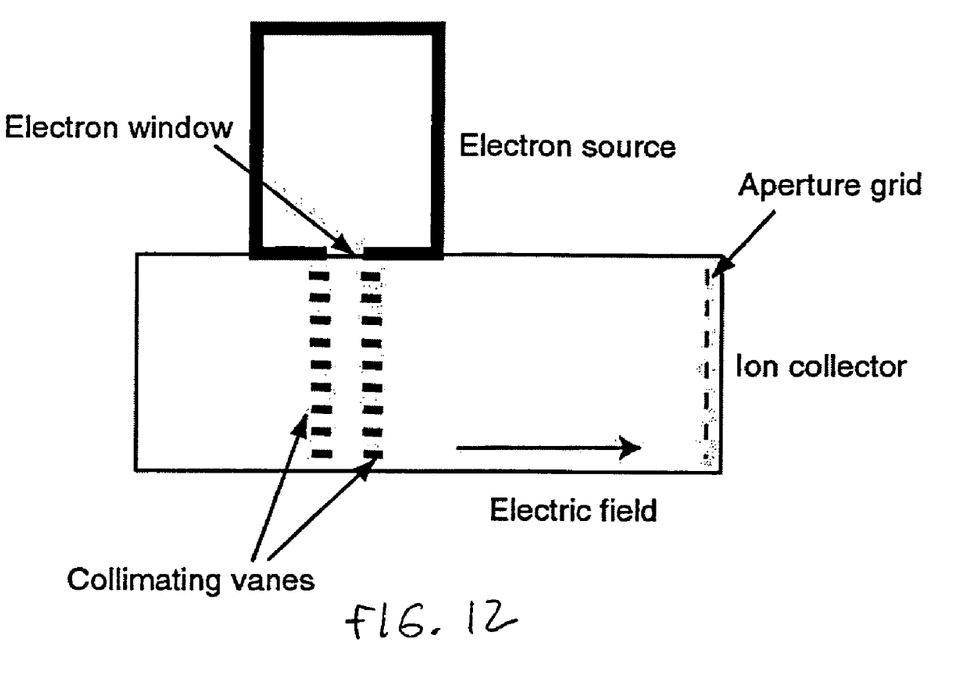
FIG. 12 is a schematic illustration showing collimating vanes to limit the width of the e-beam for cases when e-beam pulsing is used as the shutter.

A drawback of this approach is that the electron source is distributed over a volume (because of spread of the high energy electrons as they collide with the gas ions), and the separation is performed in space. Therefore, for the scheme to work, ionized gas volumes can not overlap. A method of collimating the electron beam so that the ionization region has limited length along the axis of the device is shown in FIG. 12. Multiple vanes capture those electrons that have been scattered substantially in the axial direction. This electron loss will lead to the decrease in the strength of the source (i.e., the radiation dose to the gas). The distance between the sets of vanes determines, to zeroth order, the size of the ion bunch. In order to prevent uncontrolled charging of the vanes, they need to be conducting. The ions are then extracted and drifted by the application of an axial electric field perpendicular to the direction of injection of the electron beam, as shown in FIG. 10.

Using variable ionization strength is useful for increasing the dynamic range of the device. For low concentrations, the ionization strength can be large, while for high concentrations, the ionization strength would be reduced. This has the advantage of varying the ion current in the drift region. In addition, by using high strength it is possible to have large sample gas flow rate, with improved time response.

The much larger ionization produced by the electron source can produce saturation of the signal. As the electron source is increased, it is expected that the signal from the product ions increases. The concentration of the molecules of interest can be derived from the saturation of the signal with increasing ionization source. This could make IMS devices much more useful, since present IMS devices can not be used for quantification of the concentration.

A controllable ionization source (such as an electron beam or a corona discharge) can be used for modulating the source of the ions. Space charge in the ionization region can be minimized by pulsing the ion source. Ions generated in this manner need to diffuse or drift in the presence of either an applied or self-generated field away from the ionization region, with the high mobility ions drifting or diffusing faster. Thus another method of separation is possible. This has the advantage, besides decreasing space charge, of timing the chemistry. By timing the injection time into the preconcentrator with the pulsing of the ionization source, the time of interaction between the reactive ion products and the ions of interest can be adjusted for optimal detection (sensitivity or selectivity).

The methods described above should allow the increase of IMS sensitivity by a factor of 30 to 1000 relative to present technology, and selectivity by a factor of 10.

Although the preferred method of ionization is through the use of electron beams, it should be clear to an expert in the field that the preconcentration technique can be used with any ionization source that results in large concentrations of ions, with high space charge.

The contents of all of the patents and literature articles cited herein are incorporated into this specification by reference.

What is claimed is:

1. Ion mobility spectrometer comprising:
   an enclosure for receiving a sample therewithin;
   an electron beam window for admitting an electron beam into the enclosure to ionize the sample in an ionization region;
   a shutter grid spaced apart from the ionization region; and
   means for providing sample ion preconcentration upstream of the shutter grid.

2. The spectrometer of claim 1 wherein the ion preconcentration is effective to reduce space charge resulting in a lowered threshold detection level.

3. The spectrometer of claim 1 wherein the means for providing ion preconcentration comprises a varying electric field upstream from the shutter grid.

4. The spectrometer of claim 3 further including at least one preconcentration grid upstream of the shutter grid to establish the varying electric field.

5. The spectrometer of claim 4 including a plurality of preconcentration cells.

6. The spectrometer of claim 3 wherein the varying electric field is an asymmetric field.

7. The spectrometer of claim 3 wherein the varying electric field is an asymmetric square wave.

8. The spectrometer of claim 6 wherein the asymmetric field is selected to optimize ion preconcentration.

9. The spectrometer of claim 3 wherein timing of opening of the shutter grid is synchronized with the varying electric field.

10. The spectrometer of claim 9 wherein the shutter grid is opened when sample ions are closest to the shutter grid.

11. The spectrometer of claim 4 wherein the at least one grid includes grid wires having a characteristic size and spacing less than the spacing between grids.

12. The spectrometer of claim 11 wherein the grids are a 2-dimensional pattern.

13. The spectrometer of claim 1 wherein the electron beam comes from a source using resonant acceleration of electrons.

14. The spectrometer of claim 13 wherein the resonant acceleration comes from cyclotron motion of electrons in an magnetic field.

15. The spectrometer of claim 14 wherein the magnetic field is produced by a permanent magnet.

16. The spectrometer of claim 13 wherein the electron beam source employs an RF source in the range of 500 MHz to 15 GHz.

17. The spectrometer of claim 1 wherein the electron beam comes from a source having a cold emission cathode.

18. The spectrometer of claim 1 wherein the electron beam is modulated in time.

19. The spectrometer of claim 18 wherein the opening of the shutter or the acceptance of the ion cloud in the preconcentrator region is timed with the electron beam pulse.

20. The spectrometer of claim 18 wherein the space charge is addressed by decreasing the large space charge in the ionization region, resulting in limited ion preconcentration in the ionization region.

21. The spectrometer of claim 1 wherein the electron beam window is made of diamond.

22. The spectrometer of claim 1 wherein the electron beam window is made of sapphire.

23. The spectrometer of claim 1 further including highly transparent grids in a drift region to generate uniform electric fields for increased resolution.

24. The spectrometer of claim 4 wherein the grids are manufactured using micromachining, microlithography or rapid prototyping techniques.

25. The spectrometer of claim 1 wherein quantification of sample ion concentration is determined from dependence of sample ion current on strength of ionization source.

26. The spectrometer of claim 1 wherein quantification of sample ion concentration is derived from saturation of sample ion current.

27. Ion mobility spectrometer comprising:
an enclosure for receiving a sample therewithin;
an electron beam window for admitting an electron beam into the enclosure to ionize the sample in an ionization region;
a pulsed electron beam that ionizes the gas, just upstream from a drift region, under the presence of an electric field, so that use of shutter grids is not required and a means for providing sample ion preconcentration upstream of the drift region.

28. The spectrometer of claim 27 wherein the electron beam is collimated.

29. The spectrometer of claim 28 further including vanes to collimate the electron beam.

30. Ion mobility spectrometer comprising:
an enclosure for receiving a sample there within;
means for ionizing the sample; and means for providing sample ion preconcentration upstream of a shutter grid an electric field to optimize the ionization process.

31. The spectrometer of claim 30 wherein the electric field changes the energy of secondary electrons produced by an electron beam.

32. The spectrometer of claim 30 wherein the electric field changes the energy of secondary electrons produced by a radioactive source.

33. The spectrometer of claim 30 wherein the electric field changes the energy of secondary electrons produced by an ultraviolet ionization source.

34. The spectrometer of claim 30 wherein the electric field has a value in the range of 0.8 to 8 Townsends.

35. Ion mobility spectrometer comprising:
an enclosure for receiving a sample therewithin;
a strong ionization source in the enclosure to ionize the sample in an ionization region, such that the ionization source results in high space charge;
a shutter grid spaced apart from the ionization region; and
means for providing sample ion preconcentration upstream of the shutter grid.

36. The spectrometer of claim 35 where the strong ionization source is a corona discharge.

* * * * *